United States Patent

Bell et al.

[11] Patent Number: 5,968,896
[45] Date of Patent: Oct. 19, 1999

[54] NUTRITIONAL SUPPLEMENT FOR PREOPERATIVE FEEDING

[75] Inventors: Stacey J. Bell, Belmont; R. Armour Forse, Brookline; Bruce R. Bistrian, Ipswitch, all of Mass.

[73] Assignee: Beth Israel Deaconess Medical Center, Boston, Mass.

[21] Appl. No.: 09/008,156

[22] Filed: Jan. 16, 1998

[51] Int. Cl.[6] .......................... A61K 38/00; A61K 31/70; A61K 31/715; A61K 31/595

[52] U.S. Cl. .................. 514/2; 514/23; 514/53; 514/54; 514/59; 514/60; 514/546; 514/547; 514/558; 514/560; 514/168; 514/458; 514/474

[58] Field of Search ....................... 514/2, 23, 53, 514/54, 59, 60, 546, 547, 558, 560, 168, 458, 474

[56] References Cited

U.S. PATENT DOCUMENTS

| | | | |
|---|---|---|---|
| 4,981,844 | 1/1991 | Alexander et al. | 514/21 |
| 5,234,702 | 8/1993 | Katz et al. | 426/72 |
| 5,308,832 | 5/1994 | Garleb et al. | 514/2 |
| 5,605,893 | 2/1997 | Kaufman | 514/60 |
| 5,821,217 | 10/1998 | Forse et al. | 514/2 |
| 5,843,921 | 12/1998 | Kaufman | 514/60 |

FOREIGN PATENT DOCUMENTS

| | | |
|---|---|---|
| 0183305 | 6/1986 | European Pat. Off. . |
| WO 91/18610 | 12/1991 | WIPO . |

OTHER PUBLICATIONS

Fan, S.T., et al., "Perioperative Nutritional Support in Patients Undergoing Hepatectomy for Hepatocellular Carcinoma," The New England Journal of Medicine, 331 (23) : 1547–1552 (Dec. 8, 1994).

Hirai, Y., et al., "An Enteral Elemental Diet for Infants and Children with Surgical Disorders," Journal of Parenteral and Enteral Nutrition, 4: 460–463 (Sep.–Oct. 1980).

Glotzer, D.J., et al., "Preoperative Preparation of the Colon with an Elemental Diet," Surgery, 74(5) : 703–707 (Nov. 1973).

*Primary Examiner*—Kevin E. Weddington
*Attorney, Agent, or Firm*—Hamilton, Brook, Smith & Reynolds, P.C.

[57] ABSTRACT

A nutritional supplement is described comprising approximately from about 10 to about 75 grams carbohydrate; approximately from about 5 to about 50 grams protein; approximately from about 3 to about 30 grams fat; and therapeutic amount of antioxidant, for use in weight maintenance in individuals who will undergo major surgery to prevent or reduce postoperative complications.

30 Claims, No Drawings

NUTRITIONAL SUPPLEMENT FOR PREOPERATIVE FEEDING

BACKGROUND

Postoperative complications, including infections at a surgical site and other distant nosocomial infections in high risk patients, are estimated to be between 25% and 30%. Patients particularly prone to postoperative infections are those who are malnourished prior to surgery, the elderly, and those about to undergo major gastrointestinal and non-cardiac thoracic procedures.

As early as 1987, perioperative use of parenteral nutrition was recommended by the Health and Public Policy Committee of the American College of Physicians for severely malnourished patients having major surgery, such as intra-abdominal or non-cardiac intrathoracic surgery (Health and Public Policy Committee, American College of Physicians, "perioperative parenteral Nutrition", Ann. Int. Med., 107:252–253 (1987)). Unselected use of total parenteral nutrition (TPN) is not justified, especially in mild or moderately malnourished patients because its use has been shown to be associated with an increased rate of infections and non-infectious complications (Detsky et al., "Perioperative Parenteral Nutrition: A Meta-Analysis", Ann. Int. Med., 187;107:195–203) . Around the same time, Klein and others (Klein et al., "Total Parenteral Nutrition and Cancer Clinical Trials", Cancer, 58:1378–1386 (1986).) reviewed the existing literature on cancer patients and found that the TPN is not useful if used routinely in all patients with cancer. However, they found that its preoperative use in cancer patients with gastrointestinal disease may help reduce major surgical complications and improve survival, treatment toxicity, and tumor response in patients receiving chemotherapy or radiation therapy.

Recently, thirty-three, high quality, randomized, prospective studies were reviewed on the subject of pre- and post-operative feeding, including 2,500 patients (Klein et al., "Nutritional Support in Clinical Practice: Review of Published data and recommendations for Future Research Directions", J. Parent. Ent. Nutr., 21: 133–156 (1997)). There were 13 studies including 1,250 patients who received preoperative TPN for 7 to 10 days. Most of the studies (9/13) found that patients, who received TPN and were moderately malnourished based on weight loss or depressed serum protein concentrations, had fewer postoperative complications. Those receiving preoperative TPN had 10% fewer complications and no change in mortality rates compared to those who were not preoperatively fed. There were two studies where enteral nutrition was used preoperatively for 10 days in cancer patients and postoperative complications were reduced (12%).

SUMMARY OF THE INVENTION

The invention pertains to a nutritional supplement for enteral administration which provides optimal nutrition for weight maintenance in individuals who will undergo major surgery, to provide nutrition which may reduce postoperative complications of surgery. Methods of administering the nutritional supplement to preoperative patients are described. The nutritional supplement can improve the nutritional status of the patient when administered for a period of time prior to surgery, to prepare the patient's body for major surgery through nutrition, and to improve defense capacity against postoperative infections are also described. An advantage of the methods and nutritional supplement is to provide a source of calories and protein to the patient prior to surgery to address malnourishment and to prevent further weight loss.

The nutritional supplement contains approximately from about 10 to about 75 grams carbohydrate; approximately from about 5 to about 50 grams protein; approximately from about 3 to about 30 grams fat comprising at least two different fat sources of which one is oil rich in monounsaturated fatty acids and the other is oil rich in omega-3 fatty acids; and antioxidant(s). In a preferred embodiment of the invention, the nutritional supplement contains from about 20% to about 40% of calories derived from protein; from about 25% to about 45% of calories derived from carbohydrate; and from about 26% to about 46% of calories derived from fat. The percentages are selected so as to add to 100%.

The carbohydrate can include one or more sources of carbohydrate, such as corn syrup, high fructose corn syrup, corn starch, maltodextrin, fructose, lactose, glucose,sucrose, dextrose, maltose and combinations thereof. The protein can include one or more sources of protein, such as whey protein, whey protein concentrate, whey powder, egg protein, soy protein, soy protein isolate, caseinate and combinations thereof. The fat can include one or more sources of fat, including dairy fat, coconut oil, fish oil and/or vegetable oil. Fat can be included in its natural triglyceride state as long-, medium- or short-chain triglycerides, or as structured triglycerides comprised of long-, medium- or short-chain triglycerides.

The nutritional supplement can be provided in a variety of forms, such as baked goods, puddings, confections, snack foods, ice cream, frozen confections and novelties, or non-baked, extruded foods such as bars. The nutritional supplement of the invention can be daily administered to preoperative patients to prepare them for surgery to improve nutritional status which may prevent or minimize the risks of postoperative complications. The composition is particularly suitable for use in patients who suffer from depressed host defence mechanisms, e.g. in patients who suffer from depressed host defence mechanisms as a result of post-surgical stress, cancer, chemotherapy/radiation therapy, sepsis, immunosuppressive drug therapy, HIV infection and malnutrition.

DETAILED DESCRIPTION OF THE INVENTION

The invention is drawn to a nutritional supplement that provides nutritional support (herein referred to as a "nutritional supplement") for individuals preparing for an imminent major surgical procedure, and to methods for administration of the nutritional supplement. The nutritional supplement is rich in calories and contains ingredients that have been shown to enhance/stimulate immune function. If consumed as part of a daily regimen prior to surgery, malnutrition can be addressed but not fully treated and the possible incidence of postoperative infections may be mitigated. The nutritional supplements of the invention are ideal for patients who are about to undergo major gastrointestinal or non-cardiac thoracic surgery, due to the high postoperative incidence or risk of infection.

The nutritional supplement can be made in a variety of forms, such as baked goods (e.g., cookies, brownies, fudge, cake, breads, biscuits, crackers), puddings, confections (i.e., candy), snack foods (e.g., pretzels, chips), ice cream, frozen confections and novelties, or non-baked, extruded food products such as bars. The preferred form is a non-baked extruded nutritional bar.

The nutritional supplement includes the following components: from about 10 to about 75 grams carbohydrates; from about 5 to about 50 grams protein; from about 3 to about 30 grams fat comprising at least two different fat sources of which one is oil rich in monounsaturated fatty acids and the other is oil rich in omega-3 fatty acids; and antioxidant(s). The nutritional supplement should provide a balance between total calories and glucose calories to avoid the possibility of inducing hyperglycemia; a complication which may increase infection rate.

In a preferred embodiment, the nutritional supplement comprises from about 10 to about 25 g carbohydrate; from about 10 to about 25 g protein; from about 5 to about 15 g fat; and about one half RDA amounts of antioxidants selected from the group consisting of vitamin A (as vitamin A and β-carotene), vitamin C, vitamin E and combinations thereof. In another embodiment, the amount of vitamin A is from about 250 μg to about 750 μg; the amount of β-carotene is from about 2000 μg to about 4000 μg; the amount of vitamin C is from about 25 mg to about 65 mg (60 mg=RDA); and the amount of vitamin E is from about 5 mg to about 30 (30 mg=RDA).

Preferably, the percentages of calories in the serving unit are derived from the following sources: protein, from about 20% to about 40%; carbohydrate, from about 25% to about 45%; and fat, from about 26% to about 46%. For purposes of this invention, a preferred nutritional supplement comprises the components described above as a single serving (serving unit), whereby one or a plurality of these supplement(s) is consumed daily. Alternatively, the serving unit can represent the total daily allowance of the components that comprise the nutritional supplement, for example as having the percentages defined above. The RDA amounts of antioxidants will vary depending upon the number or servings administered daily to the patient. This amount will also be dictated, in part, by patient condition.

It should be understood that the term "carbohydrate" generally includes simple carbohydrates (i.e., monosaccharides and disaccharides) and complex carbohydrates (i.e., polysaccharides). Sources of carbohydrate can include corn syrup, high fructose corn syrup, corn starch, uncooked corn starch, high amylose starch (e.g., such as those derived from but not limited to peas, barley, corn, potato, wheat, rice, tapioca, cassava, arrowroot, sage and oat), maltodextrin, fructose, lactose, sucrose, glucose, dextrose, syrups (e.g., maltitol), maltose and combinations of these. In a preferred embodiment, the nutritional supplement contains a variety of carbohydrate sources, each source selected from a different glycemic index (see Modern Nutrition in Health and Disease, eighth edition, Lea & Febiger, publishers, 1986, especially Volume 2, page 1270 and Appendix page A-135), so that glucose is released sequentially into the blood as the nutritional supplement is digested and absorbed. In a preferred embodiment, a nutritional supplement would contain carbohydrate having a low glycemic index (e.g., from less than about 70), intermediate glycemic index (e.g., from about 70 to about 80), high glycemic index (e.g., from greater than about 90) and combinations of these. Ibid. For example, the nutritional supplement can contain sucrose, which appears in the blood first; high fructose corn syrup, such as high fructose corn syrup comprising about 42% fructose and about 43% glucose, which appears next; corn syrup, which comprises glucose polymers and appears next; and uncooked corn starch, which is slowest to release into the blood and lasts up to 8 hours in the blood (i.e., having the lowest glycemic index). See Kaufman et al., U.S. Pat. No. 5,605,893 and U.S. Ser. No. 08/631,584. In another embodiment, the carbohydrate is a mixture of sucrose, maltodextrin and uncooked corn starch. Sucrose is the preferred simple carbohydrate (i.e., high glycemic index) because it provides the most desirable organoleptic properties compared to other sweeteners. Uncooked cornstarch is a preferred complex carbohydrate having a low glycemic index but should be included in food/beverage formulations which are not cooked or heat processed since the heat will break down the complex carbohydrate into simple carbohydrate (single glucose constituents), creating a high glycemic index product.

Staggering the release of sugars into the body prevents too much of an exacerbation of catecholamine excretion occurring immediately after ingestion of the nutritional supplement. A sudden burst of catecholamine may depress appetite even further. In addition, using carbohydrates that are bound to other glucose molecules in high glycemic index foods (i.e., using polysaccharides instead of solely mono- or disaccharides), it is possible to avoid raising insulin levels too quickly or too high which would in turn decrease free fatty acids, which increase serum tryptophan which, in turn, fosters an increase in the level of the brain neurotransmitter serotonin. This is particularly desirable because an increase in the brain serotonin level decreases appetite. This would exacerbate suppression of appetite. Staggering release of sugars also avoids the risk of hyperglycemia which is shown to increase the risk of infection in patients receiving total parenteral nutrition.

Sources of protein can be any suitable protein utilized in nutritional formulations and can include whey protein, whey protein concentrate, whey powder, egg, soy protein, soy protein isolate, caseinate (e.g., sodium caseinate, sodium calcium caseinate, calcium caseinate, potassium caseinate), animal and vegetable protein and mixtures thereof. When choosing a protein source, the biological value of the protein should be considered first, with the highest biological values being found in caseinate, whey, lactalbumen, egg albumen and whole egg proteins. In one embodiment, the protein source is whey protein. In another embodiment, the protein is a combination of whey protein concentrate and calcium caseinate, because these proteins have high biological value, that is, they have a high amount of the essential amino acid that is in least concentration relative to the needs of the individual. See Modern Nutrition in Health and Disease, eighth edition, Lea & Febiger, publishers, 1986, especially Volume 1, pages 30–32.

Fats and oils include but are not limited to dairy fat (e.g., butter); vegetable oil, such as canola oil, corn oil, soybean oil, sesame seed oil, safflower oil, sunflower oil, walnut oil, evening primrose oil, peanut oil, cottonseed oil, high oleic sunflower oil, rapeseed oil, olive oil, fish oil (e.g., menhaden oil, sardine oil) and mixtures thereof, all of which are examples of long-chain triglycerides; coconut oil, macadamia oil, palm oil, palm kernel oil, or mixtures thereof, all of which are examples of medium-chain triglycerides. Medium-chain triglycerides are rapidly taken up and used by the body (see, e.g., U.S. Pat. No. 4,871,768 of Bistrian et al. for examples of suitable fat sources; the entire teachings are incorporated herein by reference). The oils can be used in their natural states; alternatively, structured triglycerides, which can be either randomly re-esterified or specifically reesterified, can be generated from two or more oils and used as a fat source. Structured triglycerides can contain long-chain triglycerides, medium-chain triglycerides, short-chain, triglycerides, or combinations thereof. In a preferred embodiment, the source of fat is canola oil. See U.S. Pat. No. 5,260,336 to Forse and Mascioli and Yaqoob et al., *Am J. Clin. Nutr.*, 67:129–35 (1998) for examples of monounsaturated fats; the entire teachings of which are incorporated herein by reference.

Fats are the most calorically dense nutrient; however, fat calories, and particularly longer chain fats or more saturated fats, are typically the poorest absorbed, compared to protein and carbohydrate calories (Modern Nutrition in Health and Disease, eighth edition, Lea & Febiger, publishers, 1986, especially Volume 1, pages 82-83) . In order for weight gain to occur, calories need to be absorbed. Thus, in one embodiment, the fat includes fish oil, butter, canola oil and structured triglycerides, which have been shown to be well absorbed in critically ill patients who have difficulty absorbing fats (Kenler, A.S. et al., Annals of Surg., 223(3):316–333 (1996); Christensen et al., Am. J. Clin. Nutr., 61:56–61 (1995)).

Preferably, the nutritional supplement provides approximately 200 kcal per unit serving, because it is designed to supplement regular meals, rather than to replace them. The objective of the invention is to supplement the diet of an individual, and not to depress the individual's appetite at meals themselves; the 200 kcal size is optimal to meet this objective. Further, a nutritional bar that provides 200 kcal per serving makes it easy for the individual and/or health care provider to track calories. However, other unit serving sizes are embraced by the invention, e.g. from about 100 to about 300 kcal/serving.

The nutritional supplement comprises one or a combination of antioxidants in therapeutic amounts. Antioxidants suitable for use in this invention include, but are not limited to, vitamin A, vitamin C, vitamin E, β-carotene, zinc, chromium, selenium and herbs, such as ginkgo biloba, ginsing. A "therapeutic amount" is intended herein to be an amount which is sufficient to provide a therapeutic benefit to the patient. The amount of antioxidant(s) per unit serving are a matter of design and will depend upon the total number of unit servings of the nutritional supplement daily administered to the patient. The total amount of antioxidant(s) will also depend, in part, upon the condition of the patient. Preferably the amount of antioxidant(s) will be a fraction or multiplier of the RDA amounts. For example, the nutritional supplement will comprise 50% RDA antioxidants per unit dosage and the patient will consume two units per day.

It is desirable to daily administer the nutritional supplement from about seven to about ten days prior to surgery in moderately to severely malnourished patients. Patients who tend to be malnourished or undernourished, include, but are not limited to, those suffering from post surgical stress, cancer, chemotherapy/radiation therapy, sepsis, immunosuppressive drug therapy, HIV infection and malnutrition. The nutritional supplements of this invention can be used alone or in combination with parenteral nutritional, enteral nutritional supplements consumed orally or administered by tube, or regular diet.

The nutritional supplement can also contain other ingredients such as one or a combination of other vitamins, minerals, antioxidants, fiber and other dietary supplements. Selection of one or several of these ingredients is a matter of formulation design, consumer preference and end-user. The amount of these ingredients added to the nutritional supplements of this invention are readily known to the skilled artisan and guidance to such amounts can be provided by the U.S. RDA doses for children and adults. Vitamins and minerals that can be added include, but are not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; Vitamin $D_3$; cyanocobalamin; sodium selenite; copper sulfate; Vitamin A; Vitamin E; Vitamin $B_6$ and hydrochloride thereof; Vitamin C; inositol; Vitamin $B_{12}$; potassium iodide.

Flavors, coloring agents, spices, nuts and the like can be incorporated into the product. Flavorings can be in the form of flavored extracts, volatile oils, chocolate flavorings, peanut butter flavoring, cookie crumbs, crisp rice, vanilla or any commercially available flavoring. Examples of useful flavorings include but are not limited to pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as balm oil, bay oil, bergamot oil, cedarwood oil, cherry oil, walnut oil, cinnamon oil, clove oil, or peppermint oil; peanut butter, chocolate flavoring, vanilla cookie crumb, butterscotch or toffee. In a preferred embodiment, the nutritional supplement contains cocoa or chocolate.

Emulsifiers may be added for stability of the final product. Examples of suitable emulsifiers include, but are not limited to, lecithin (e.g., from egg or soy), and/or mono- and di-glycerides. Other emulsifiers are readily apparent to the skilled artisan and selection of suitable emulsifier(s) will depend, in part, upon the formulation and final product.

Preservatives may also be added to the nutritional supplement to extend product shelf life. Preferably, preservatives such as potassium sorbate, sodium sorbate, potassium benzoate, sodium benzoate or calcium disodium EDTA are used.

In addition to the carbohydrates described above, the nutritional supplement can contain artificial sweeteners, e.g., saccharides, cyclamates, aspartamine, aspartame, acesulfame K, and/or sorbitol. Such artificial sweeteners can be desirable if the nutritional supplement is intended for an overweight or obese individual, or an individual with type II diabetes who is prone to hyperglycemia.

In one embodiment, the nutritional supplement is a nonbaked, extruded food bar that provides 200 kcal/unit serving and has the following characteristics:

about 17 grams carbohydrate from sucrose, maltodextrin and uncooked corn starch;

about 15 grams protein from whey;

about 8 grams fat comprising fish oil, butter, canola oil and MCT oil as a structured lipid or physical mixture; and about 50 percent RDA of antioxidants selected from the group consisting of vitamin A (comprising about 50 μg vitamin A and about 3000 μg β-carotene), vitamin C (about 60 mg), vitamin E (about 10 mg as alpha-tocopheryl acetate).

To manufacture such a food bar, the liquid ingredients are cooked; the dry ingredients are added with the liquid ingredients in a mixer and mixed until the dough phase is reached; the dough is put into an extruder, and extruded; the extruded dough is cut into appropriate lengths; and the product is cooled.

For manufacture of other foods or beverages, the ingredients comprising the nutritional supplement of this invention can be added to traditional formulations or they can be used to replace traditional ingredients, particularly the carbohydrate components. Those skilled in food formulating will be able to design appropriate foods/beverages with the objective of this invention in mind.

The nutritional supplement can be consumed at any time of day, as part of a meal or caloric supplementation program. The nutritional supplement is intended to be administered up to two weeks prior to surgery, from about 7 to about 10 days being preferred and two weeks being optional. See also USSN 08/966,829, filed Nov. 10, 1997, the teachings of which are incorporated herein by reference in their entirety, which teaches nutritional supplements that can be used by individuals who are affected by a disease or condition that prevents intake of adequate nutrition or who require increased calories and/or protein.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A nutritional supplement comprising approximately from about 10 to about 75 grams carbohydrate; approximately from about 5 to about 50 grams protein; and approximately from about 3 to about 30 grams fat comprising at least two different fat sources of which one is oil rich in monounsaturated fatty acids and the other is oil rich in omega-3 fatty acids; and therapeutic amount of antioxidant.

2. The nutritional supplement of claim 1 wherein the supplement comprises from about 10 to about 25 grams carbohydrate.

3. The nutritional supplement of claim 1 wherein the supplement comprises from about 10 to about 25 grams protein.

4. The nutritional supplement of claim 1 wherein the supplement comprises from about 5 to about 15 grams fats.

5. The nutritional supplement of claim 1, the carbohydrate comprises carbohydrate having a high glycemic index; carbohydrate having an intermediate glycemic index; and carbohydrate having a low glycemic index.

6. The nutritional supplement of claim 1, wherein the carbohydrate comprises at least one carbohydrate source selected from the group consisting of: corn syrup, high fructose corn syrup, corn starch, uncooked corn starch, high amylose starch, maltodextrin, sucrose, fructose, lactose, glucose, dextrose, maltose and combinations thereof.

7. The nutritional supplement of claim 1, wherein the carbohydrate comprises more than one carbohydrate source, each carbohydrate source being selected from the group consisting of: corn syrup, high fructose corn syrup, corn starch, uncooked corn starch, high amylose starch, maltodextrin, fructose, sucrose, lactose, glucose, dextrose, maltose and combinations thereof.

8. The nutritional supplement of claim 7, wherein the carbohydrate comprises sucrose, maltodextrin and uncooked corn starch.

9. The nutritional supplement of claim 1, wherein the protein comprises at least one protein source selected from the group consisting of: whey protein, whey protein concentrate, whey powder, egg protein, soy protein, soy protein isolate, sodium caseinate, sodium calcium caseinate, calcium caseinate, potassium caseinate and combinations thereof.

10. The nutritional supplement of claim 1, wherein the protein comprises more than one protein source, each protein source being selected from the group consisting of: whey protein, whey protein concentrate, whey powder, egg protein, soy protein, soy protein isolate, sodium caseinate, sodium calcium caseinate, calcium caseinate, potassium caseinate and combinations thereof.

11. The nutritional supplement of claim 10, wherein the protein source is whey protein.

12. The nutritional supplement of claim 1, wherein the fat is selected from the group consisting of: dairy fat, structured triglycerides, long-chain triglycerides, medium-chain triglycerides, short-chain triglycerides, canola oil, corn oil, soybean oil, sesame seed oil, safflower oil, sunflower oil, high oleic sunflower oil, rapeseed oil, olive oil, sardine oil, walnut oil, menhaden oil, evening primrose oil, peanut oil, cottonseed oil, coconut oil, macadamia oil, palm oil, palm kernel oil and combination thereof.

13. The nutritional supplement of claim 12, wherein the fat comprises canola oil, fish oil, vegetable oil, dairy fat and medium-chain triglycerides.

14. The nutritional supplement of claim 1, wherein the antioxidant is selected from the group consisting of vitamin A, vitamin E, vitamin C, selenium, herbs and combination thereof.

15. The nutritional supplement of claim 1, wherein the form of the nutritional supplement is selected from the group consisting of: nutritional beverage, baked good, pudding, confection, snack food, ice cream, frozen confection, and non-baked, extruded food product.

16. The nutritional supplement of claim 15, wherein the non-baked, extruded food product is a bar.

17. A nutritional supplement of claim 1 having approximately 200 kcals.

18. A nutritional supplement comprising: approximately from about 10 to about 75 grams carbohydrate, wherein the carbohydrate comprises at least one carbohydrate source selected from the group consisting of: corn syrup, high fructose corn syrup, corn starch, uncooked corn starch, high amylose starch, maltodextrin, sucrose, fructose, lactose, glucose, dextrose, maltose and combination thereof;

approximately from about 5 to about 50 grams protein, wherein the protein comprises at least one protein source selected from the group consisting of: whey protein, whey protein concentrate, whey powder, egg protein, soy protein, soy protein isolate, sodium caseinate, sodium calcium caseinate, calcium caseinate, potassium caseinate and combination thereof;

approximately from about 3 to about 30 grams fat, wherein the fat comprising at least two different fat sources of which one is oil rich in monounsaturated fatty acids and the other is oil rich in omega-3 fatty acids and is selected from the group consisting of: dairy fat, structured triglycerides, long-chain triglycerides, medium-chain triglycerides, canola oil, corn oil, soybean oil, sesame seed oil, safflower oil, sunflower oil, high oleic sunflower oil, rapeseed oil, olive oil, menhaden oil, sardine oil, evening primrose oil, peanut oil, cottonseed oil, coconut oil, macadamia oil, palm oil, palm kernel oil and combinations thereof; and therapeutic amount of antioxidants selected from the group consisting of vitamin A, vitamin C, vitamin E and combinations thereof.

19. The nutritional supplement of claim 18, wherein the carbohydrate comprises sucrose, maltodextrin and uncooked corn starch; wherein the protein source comprises whey protein wherein the fat comprises canola oil, dairy fat, medium-chain triglycerides and fish oil as the source of omega-3 fatty acid; and the antioxidants are vitamin A, vitamin C and vitamin E.

20. The nutritional supplement of claim 19, which is a non-baked, extruded food product.

21. A nutritional supplement comprising approximately from about 10 to about 25 grams carbohydrate; approximately from about 10 to about 25 grams protein; approximately from about 5 to about 15 grams fat; approximately from about 250 µg to about 750 µg vitamin A; approximately from about 2000 µg to about 4000 µg β-carotene; approximately from about 25 mg to about 65 mg vitamin C; and approximately from about 5 mg to about 30 mg vitamin E.

22. An extruded, nonbaked food bar comprising from about 10 to about 75 grams carbohydrate; approximately from about 5 to about 50 grams protein; approximately from about 3 to 30 grams fat comprising at least two different fat sources of which one is oil rich in monounsaturated fatty acids and the other is oil rich in omega-3 fatty acids; and therapeutic amount of antioxidant.

23. The food bar of claim 22 wherein the carbohydrate is from about 10 to about 25 grams; the protein is from about 10 to about 25 grams; the fat is from about 5 to about 15 grams; and about 50% RDA each of vitamin A, vitamin C and vitamin E.

24. The food bar of claim 22 having approximately 200 calories.

25. The food bar of claim 24 comprising sucrose, maltodextrin, corn starch, canola oil, whey protein, fish oil, vegetable oil, dairy fat and medium-chain triglycerides.

26. A method of providing nutritional supplementation to a preoperative patient, comprising administering to the patient, for a sufficient period of time prior to surgery, a nutritional supplement comprising approximately from about 10 to about 75 grams carbohydrate; approximately from about 5 to about 50 grams protein; approximately from about 3 to about 30 grams fat comprising at least two different fat sources of which one is oil rich in monounsaturated fatty acids and the other is oil rich in omega-3 fatty acids; and therapeutic amounts of antioxidant.

27. The method of claim 26, wherein the carbohydrate comprises sucrose, maltodextrin, corn starch; canola oil, whey protein, fish oil, vegetable oil, dairy fat and medium-chain triglycerides.

28. A method of reducing postoperative infections in a surgical patient comprising administering to the patient the nutritional supplement of claim 1, for a sufficient period of time prior to surgery.

29. A method of preventing weight loss and/or malnutrition in a patient in imminent need of surgery, comprising administering to the patient the nutritional supplement of claim 1, for a sufficient period of time prior to surgery.

30. A method of improving the nutritional status of a patient in imminent need of surgery, comprising administering to the patient the nutritional supplement of claim 1, for a sufficient period of time prior to surgery.

* * * * *